(12) United States Patent
Bunn et al.

(10) Patent No.: US 6,288,025 B1
(45) Date of Patent: Sep. 11, 2001

(54) PROTEASE INHIBITORS FOR USE IN THE TREATMENT OF PSORIASIS

(75) Inventors: Clive Leighton Bunn, West Ryde; Phillip John Sharp, Glebe, both of (AU)

(73) Assignee: Biotech Australia Pty Limited, Roseville (AU)

( * ) Notice: Subject to any disclaimer, the term of this patent is extended or adjusted under 35 U.S.C. 154(b) by 0 days.

(21) Appl. No.: 09/368,164

(22) Filed: Aug. 5, 1999

(30) Foreign Application Priority Data

Aug. 5, 1998 (AU) .................................................. PP 5087

(51) Int. Cl.[7] .............................. A61K 38/00; C07K 5/00; C07K 7/00
(52) U.S. Cl. ................................. 514/2; 514/12; 530/300; 424/185.1
(58) Field of Search ........................ 514/2, 12; 530/300; 424/185.1

(56) References Cited

U.S. PATENT DOCUMENTS

| | | | |
|---|---|---|---|
| 5,204,807 | 4/1993 | Simkins et al. | 361/399 |
| 5,290,762 * | 3/1994 | Lezdey et al. | 514/8 |
| 5,298,400 | 3/1994 | Whitfeld et al. | 435/69.8 |
| 5,403,482 | 4/1995 | Steere et al. | 210/489 |
| 5,444,153 | 8/1995 | Goss et al. | 424/141 |
| 5,462,857 | 10/1995 | Campbell et al. | 435/7.21 |
| 5,486,602 | 1/1996 | Sambrook et al. | 536/23.2 |
| 5,550,042 | 8/1996 | Sambrook et al. | 435/172.1 |
| 5,728,564 | 3/1998 | Sambrook et al. | 435/215 |
| 5,807,829 * | 9/1998 | Gyorkos et al. | 514/18 |

FOREIGN PATENT DOCUMENTS

| | | |
|---|---|---|
| 616555 | 3/1990 | (AU) . |
| 0410 411 A2 | 7/1990 | (EP) . |
| 6279316 | 10/1994 | (JP) . |
| 91/03556 | 3/1991 | (WO) . |
| 91/09124 | 6/1991 | (WO) . |
| 99/49887 | 10/1999 | (WO) . |

OTHER PUBLICATIONS

Lotti Et Al., *Pharmacology and Therapeutics*, vol. 29, No. 7, Sep. 1990, pp. 528–530.*

J. Baird et al., "mRNA for Tissue–Type Plasminogen Activator Is Present . . . But Is Not Detected in Normal Epidermis", J. Invest. Derma., vol. 95, No. 5, 1990, pp. 548–552.

P. J.. Jensen, Ph.D. et al., "Epidermal Plasminogen Activator is Abnormal in Cutaneous Lesions", J. Invest. Derma., vol. 90, No. 6, 1988, pp. 777–782.

E. Kruithof et al., "Bliological and Clinical Aspects of Plasminogen Activator Inhibitor Type 2", Blood, vol. 86, No. 11, 12/95, pp. 4007–4024.

T. Lotti et al., "Antisoriatic Therapies Inhibit Epidermal Plasminogen Activator Activity", Pharm. & Therapeu. vol. 29, No. 7, 9/90, pp. 528–530.

B. Lyons–Giodano et al., "Expression of plasminogen activator inhibitor type 2 in normal and psoriatic Epidermis", Histochemistry (1994), 101, pp. 105–112.

* cited by examiner

*Primary Examiner*—Avis M. Davenport
(74) *Attorney, Agent, or Firm*—Foley & Lardner

(57) ABSTRACT

Psoriasis may be treated by topical administration of a urokinase inhibitor, such as PAI-2, or a combination of protease inhibitors, such as PAI-2 with other serine protease inhibitors and/or with protease inhibitors such as inhibitors of metalloproteinases, acid proteases, and thiol proteases.

20 Claims, 1 Drawing Sheet

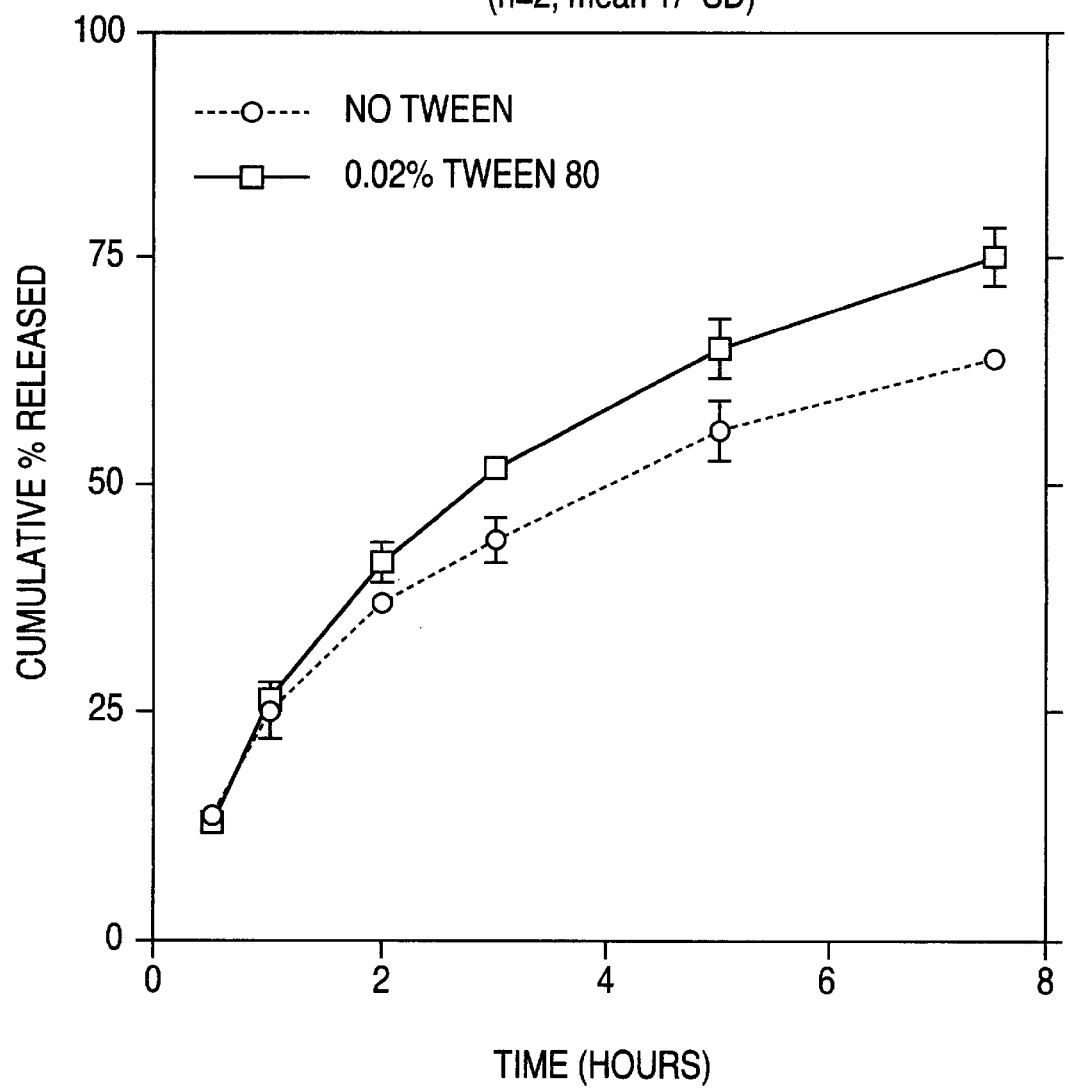

PROTEASE INHIBITORS FOR USE IN THE TREATMENT OF PSORIASIS

BACKGROUND OF THE INVENTION

Psoriasis is a chronic skin disease characterized by erythematous plaques of thickened, reddening, and scaling skin. Psoriasis affects about 2% of the population. Onset occurs most often in early adult life, but also may begin in childhood or in aged people. Severity of the disease varies and is usually characterized by alternating periods of remission and flare-up. In more serious cases, psoriasis can affect up to 90% of the skin and can be life threatening At the cellular level, psoriasis is characterized by a hyper proliferation of epidermal keratinocytes, accompanied by infiltration of T lymphocytes and other immune system cells, the latter giving rise to inflammation similar to that in autoimmnune diseases. The epidermal turnover time for a keratinocyte to travel from the basal cell layer to the stratum corneum normally is 14 days, during which the keratinocyte undergoes a complex series of changes in gene expression resulting in cell death—"terminal differentiation." In a psoriasis patient, the epidermal turnover time is 2 days, with marked increase in proliferation of keratinocytes, which are subsequently shed in a relative immature, or less differentiated, form.

Currently, there is no long-term cure for psoriasis. Treatments include coal tar preparations (natural coal tar or the distillate anthralin), topical corticosteroids, mechanical treatments to remove scale, and antimetabolites such as methotrexate. The photosensitizing drug, psoralen, combined with long wavelength ultraviolet light (PUVA), and synthetic retinoids also are used. While mild to moderate cases can be treated somewhat effectively, more extensive cases are difficult and tend to be resistant to either topical therapy or ultraviolet phototherapy. Moreover, systemic use of traditional antipsoriatic drugs, or prolonged use of topical steroids, can lead to undesirable side effects or rebound worsening of psoriasis.

Genetic analysis indicates that at least some forms of psoriasis include an inherited component, and intense efforts are underway to locate "psoriasis susceptibility genes." The similarity to autoimmune diseases, and the increased incidence of HLA-13, HLA-17, HLA-Cw6, and HLA-DRw7 in affected individuals has focused attention on on immunomodulatory strategies and the development of new drugs which decrease T-cell activation or deplete activated T-cell pools. Research has been severely impeded, however, by the lack of an animal model which reflects all the diverse clinical and cellular changes present in psoriatic plaques.

An alternative approach to immune modulation that may avoid potential side effects from drugs of this type is to focus on the abnormal keratinocyte differentiation in psoriasis. Keratinocyte maturation is associated with the production of proteinases, which can degrade the surrounding extracellular matrix to allow cell migration to the superficial layers and activate cells to divide, either directly, or indirectly by activating cytokines precursors. At terminal differentiation, the formation of a stable stratum corneum would require that the activity of such proteinases be down-regulated. Several proteinases, such as plasminogen activator and cathepsin B, have been shown to be present in normal skin, and it is possible that the cellular pathophysiology in psoriasis may result from excessive and unregulated levels of proteinases.

In psoriasis, abnormalities in the expression of both urokinase plasminogen activator (u-PA) and tissue plasminogen activator (t-PA) expression have been observed. The most dramatic change is the greatly enhanced t-PA expression in suprabasal epidermis. Jensen et al., *J. Invest. Dermatol.* 90(6):777–782 (1988). Baird et al., *J. Invest. Dermatol.* 95(5):548–552 (November 1990). Biopsies from 40 patients with psoriasis before and after topical (anthralin, corticosteroid) and systemic (PUVA) treatments by the autohistographic fibrin film method showed that both u-PA and t-PA immunoreactivity were present in psoriatic patches but absent from normal and treated, clear skin. Lotti et al., *Int. J. Dermatol.* 29(7):528–530 (1990). Moreover, increase in PAI-2 in psoriatic epidermis, in the same suprabasal areas as t-PA suggests that PAI-2 has a protective role in cutaneous pathologies that elicit abnormal wound healing patterns. Lyons-Giordano et al., "Expression of plasminogen activator inhibitor type 2 in normal and psoriatic epidermis," *Histoclemistry* 101(2):105–112 (February 1994).

It is apparent, therefore, that new methods and compositions for treating psoriasis are greatly to be desired. In particular, it would be desirable to develop new methods and compositions for treating psoriasis that regulate the plasminogen activator/inhibitor system and in particular that utilize plasminogen activator inhibitors.

SUMMARY OF THE INVENTION

The present invention relates to the use of a urokinase inhibitor for treating psoriasis. Thus, the present invention provides a method of treating psoriasis comprising administering to a patient in need thereof an effective amount of a urokinase inhibitor, wherein said inhibitor is topically administered to the affected area of the skin. In one embodiment of the invention, the urokinase inhibitor is selected from the group consisting of PAI-2, a variant thereof having plasminogen activating inhibitory properties, a derivative of PAI-2, and a variant of said derivative.

According to one aspect of the invention, the derivative is obtained by biochemical modification of PAI-2, wherein said modification is selected from the group consisting of chemical linking with polyethylene glycol, phosphate group attachment, sulfate group attachment, peptidase treatment, treatment with a sugar chain-modifying enzyme, and treatment with a sugar attachment enzyme. In one embodiment, the variant is obtained by deletion or addition of amino acid residues from the amino terminal end of PAI-2. In another embodiment, the variant is obtained by deletion or addition of amino acid residues from the carboxy terminal end of PAI-2.

According to another aspect of the invention, the urokinase inhibitor is administered in a gel formulation. In one embodiment, the gel is a cellulose gel further comprising a detergent. In another embodiment of the invention, the detergent is Tween-80.

According to yet another aspect of the invention, the PAI-2 is administered in a range of 0.1–2000 $\mu g/cm^2$ of wound. According to yet another aspect of the invention, the PAI-2 is administered at least once a day for at least five days.

The present invention also provides a method of treating psoriasis comprising administering to a patient in need thereof an effective amount of a therapeutic agent comprising PAI-2 and at least one other serine protease inhibitor, wherein said therapeutic agent is topically administered to the affected area of the skin. In one embodiment, the other serine protease inhibitor is a uPA inhibitor.

According to one aspect of the invention, the therapeutic agent further comprises a protease inhibitor selected from the group consisting of thiol protease inhibitors, acid protease inhibitors, and metalloproteinase inhibitors. In one embodiment, these protease inhibitors are co-administered with PAI-2.

The present invention further relates to a pharmaceutical composition comprising PAI-2 in a gel containing a detergent. According to one aspect of the invention, the pharmaceutical composition comprises PAI-2 and at least one other serine protease inhibitor. According to another aspect of the invention, the pharmaceutical composition further comprising a protease inhibitor selected from the group consisting of thiol protease inhibitors, acid protease inhibitors, and metalloproteinase inhibitors. In one embodiment, the detergent is Tween-80. In another embodiment, the gel is a cellulose gel. In another embodiment, the gel contains at least one further component that reduces the formation of aggregates, enhances the stability of PAI-2, and that may act as a penetration enhancer. In a preferred embodiment, that component is propylene glycol.

Other objects, features and advantages of the present invention will become apparent from the following detailed description. It should be understood, however, that the detailed description and the specific examples, while indicating particular embodiments of the invention, are given by way of illustration only, since various changes and modifications within the spirit and scope of the invention will become apparent to those skilled in the art from this detailed description.

BREF DESCRIPTION OF THE FIGURES

FIG. 1 shows the enhanced release of PAI-2 from a cellulose gel in the presence of Tween 80.

DETAILED DESCRIPTION OF PREFERRED EMBODIMENTS

The present invention provide s compositions comprising a urokinase inhibitor that are useful for treating psoriasis. In a preferred embodiment, the inhibitor is provided as a topical agent. The invention also encompasses compositions comprising a urokinase inhibitor in conjunction with another protease inhibitor for treating psoriasis. In addition, the present invention provides methods for treating psoriasis comprising topical application of the previously described compositions to the affected area of the skin.

In a preferred embodiment, plasminogen activator inhibitor 2 (PAI-2) is the topical agent. The properties of PAI-2 are described in detail in Kruithof et al., "Biological and Clinical Aspects of Plasminogen Activator Type II," *Blood* 86:4007 (1995). Briefly, PAI-2 is a component of the plasminogen activator (PA) system. The PA system has numerous functions, including regulation of extracellular proteolysis in a wide variety of physiological processes, such as tissue remodeling, cell migration, wound healing, and angiogenesis.

Plasminogen activators (PA) are serine proteases that convert plasminogen into plasmin, a trypsin-like serine protease, that is responsible not only for the degradation of fibrin, but also contributes to the degradation and turnover of the extracellular matrix. Plasmin can be formed locally at sites of inflammation and repaired by limited proteolysis of its inactive precursor, plasminogen, which circulates in plasma and interstitial fluids. Plasminogen is activated by either urokinase-type plasminogen activator (u-PA) or tissue-type plasminogen activator (t-PA). These catalytic reactions generally take place at the plasma membrane (u-PA) or on a fibrin surface (t-PA). These activating enzymes are produced by a wide range of mesenchymal, epithelial and endoepithelial cells in response to a variety of cytokines and growth factors. Activated plasmin can degrade a wide range of substrates including extracellular matrix macromolecules (excluding collagens) and fibrin. The activities of plasmin and its activating proteinases are regulated extracellularly through a number of protease inhibitors including PAI-2 and plasminogen activator inhibitor-1 (PAI-1).

The present inventors have found that the topical administration of a compound selected from the category of urokinase inhibitors, such as PAI-2, results in a lessening of psoriatic plaque thickness, redness and scaling associated with psoriatic lesions, and erythema. In a preferred embodiment of the invention, the serine protease inhibitor PAI-2 is used. Variants of PAI-2, which have substantially the same amino acid sequence of PAI-2 and which inhibit plasminogen activators, also can be used in the compositions of the present invention. That is, a "variant of PAI-2" is a protein having substantially the amino acid sequence of PAI-2, to the extent that residues of the PAI-2 amino acid sequence are deleted, added or substituted, naturally or artificially, but the characteristic inhibitory activity of PAI-2 is not lost. Assays for PAI-2 activity, well known in the art, are readily applicable to the screening of putative variants in this regard.

Thus, conservative, semi-conservative, and other amino acid substitutions are contemplated by the present invention, as long as they do not so reduce activity such that the affected polypeptide is therapeutically ineffective in this context. Sequences in the N-terminal and C-terminal regions of naturally occurring and recombinant PAI-2 may vary— causing an increase or decrease in the number of amino acid residues—depending on the production conditions. These variations specifically are within the scope of the present invention. The skilled artisan will recognize that other active variants of PAI-2 also may be used in the invention, provided that they retain the characteristic protease inhibitor properties of PAI-2. Variants of PAI-2 and methods of making such variants also are described in U.S. Pat. Nos. 5,728,564, 5,550,042, 5,486,602, 5,444,153, and 5,304,482.

Also suitable as the active ingredient, pursuant to the present invention, are derivatives that can be produced by chemically or biochemically modifying PAI-2 or a PAI-2 variant. Exemplary of such derivatives are compounds obtained (A) by chemically linking polyethylene glycol or an analogue thereof, (B) by attaching phosphate or sulfate groups, (C) by treatment with a peptidase, such as an endopeptidase, and (D) by treatment with a sugar chain-modifying enzyme or a sugar chain-attaching enzymne, such as sialidase. Derivatives prepared in this fashion can be assayed for protease inhibitor activity by methods that are well known in the art. See, for example, Fersht, ENZYME STRUCTURE AND MECHANISM, 2d ed. W. H. Freeman and Co., 1985, and references therein.

The protease inhibitor, such as PAI-2 or the PAI-2 variants and derivatives described herein (herein collectively referred to as "PAI-2") may be administered topically to patients in any suitable physiologically acceptable vehicle, for example, in phosphate-buffered saline (PBS) solution. Other vehicles are well known in the art and are described, for example, in REMINGTON'S PHARMACEUTICAL SCIENCES, 18th Edition, Mack Publishing Company, Easton, Pa. (1990).

The protease inhibitor can be applied to the wound daily, or more or less frequently as required. The skilled artisan will recognize that optimization of dosage regimens for particular applications is well known in the art, for example as described in REMINGTON'S, supra. A typical daily dosage of inhibitor will be about 20 µg per cm² of the affected site on the skin, although it will be recognized that this amount may be varied, and concentrations of 0.1–2000 µg/cm² advantageously may be used. For example, more severe cases of psoriasis may require concentrations of 500 µg/cm² applied multiple times per day, such as, for example, 2, 3, or 4 times daily. For less severe cases, or those which are responding well to higher doses, the dose may be lowered. For example, the protease inhibitor dose may be lowered sequentially to, for example, 100, 10, 1, or 0.1 µg/cm². In addition, the application of the inhibitor may be made less frequently, such as from 4 to 1 times daily. PAI-2 does not appear to have systemic toxicity and, therefore, even higher doses may be used if necessary. If necessary, the systemic concentration of PAI-2 can be measured using an ELISA test, and the dosage of PAI-2 can be adjusted accordingly. The toxicity and systemic concentration of other suitable inhibitors can be measured by methods known to those of skill in the art.

The concentration of inhibitor in the vehicle used for application to the patient advantageously is about 1 mg/ml, although higher or lower concentrations can be used if necessary. For example, concentrations as low as about 0.1 mg, or as high as the limit of solubility of inhibitor in the vehicle, may be used.

The inhibitor may be applied via short or long term application. Vehicles such as PBS are suitable for short term application of the inhibitor. For longer term application, use of a slow release vehicle is preferred. For example, a gel formulation can be used for effective delivery of the inhibitor. Cellulose derivatives previously have been described to be compatible in gel formulations with certain proteins such as EGF, TGF-α, PDGF and FGF. Proteins in these formulations tend to aggregate over time, however, which is deleterious for the present application. This aggregation is manifested as opalescence or turbidity of the gel, and leads to lower activity of the active protein ingredient, and slower release of the protein from the gel, due to the increased size of the aggregates.

The present inventors have overcome this aggregation problem by the addition of a small amount (up to, and including, 0.05%) of detergent to a inhibitor/cellulose polymer gel. This results in a gel that has substantially improved clarity. The advantages of this gel are shown in more detail in Example 2, infra. Detergents such as Tween 80 or Genapol PF10 may be used. The skilled artisan also will recognize that other detergents may also successfully be used.

Unexpectedly, the present inventors have found that, in addition to reducing aggregation in the gel, use of Tween 80 at 0.02% results in enhanced release of the inhibitor from an inhibitor/Natrosol-containing gel. These experiments are described below in Example 2. The present inventors further have found that addition of up to 10% propylene glycol to the gel also reduces the formation of aggregates and enhances the stability of the PAI-2 in the gel. The propylene glycol further appears to enhance penetration of the PAI-2 into the skin.

In another embodiment of the invention, PAI-2 is used in conjunction with at least one other protease inhibitor. For example, PAI-2 may be used in conjunction with another serine protease inhibitor, such as amiloride, or a derivative thereof.

In yet another embodiment, PAI-2 is used in conjunction with at least one inhibitor of metalloproteinases, acid proteases and/or thiol proteases. For example, PAI-2 may be used in conjunction with one or more of ethylene diamine tetraacetic acid (EDTA), pepstatin, and N-ethyl maleimide (NEM).

In still another embodiment, PAI-2 is used in conjunction with a combination of at least one other protease inhibitor and at least one other inhibitor of metalloproteinases, acid proteases and/or thiol proteases.

Inhibitors of serine and thiol proteases, and of acid proteases and metalloproteases, are well known in the art, and many are commercially available, for example, from Boehringer Mannheim (Indianapolis, Ind.), Promega (Madison, Wis.), Calbiochem (La Jolla, Calif.), and Life Technologies (Rockville, Md.). Other inhibitors are described in well-known texts on enzymology, for example, Fersht, ENZYME STRUCTURE AND MECHANISM, 2d ed. W. H. Freeman and Co., 1985, and references therein.

The other inhibitors may be applied before or after, or simultaneously with, PAI-2 treatment. The inhibitors also may be applied more or less frequently than PAI-2. In particular, inhibitors that are more rapidly degraded may be applied more frequently than more stable inhibitors. Conversely, more stable inhibitors can be applied less frequently. The skilled artisan will recognize that straightforward assays of inhibitor stability may be used to gauge the frequency of administration of the inhibitors.

Advantageously, the other inhibitors may be applied in the same vehicle as the PAI-2, although this is not essential for efficacy. In particular, the inhibitors may be applied in the same gel vehicle that may be used for PAI-2, as described above. If the inhibitors are not applied in the same vehicle as PAI-2, then they can be applied in any pharmaceutically acceptable vehicle, as described, for example, in REMINGTON'S, supra.

The present invention, thus generally described, will be understood more readily by reference to the following examples, which are provided by way of illustration and are not intended to be limiting of the present invention.

EXAMPLE 1

Topical Application of PAI-2 Gel (1 mg/g) for the Treatment of Psoriasis

A. Basic Study Design

A double-blind, placebo controlled randomized study was conducted to determine the safety, tolerability and efficacy of topically applied PAI-2 gel for the treatment of mild to moderate psoriasis. A total of 22 patients were enrolled in the study: 13 male and 9 female, with a mean age of 42 years (range 18–64 years). The duration of the disease in patients who entered the study was, on average, 17 years (range 3–34 years). Of the 22 patients who commenced the trial 14 patients had no treatment on their trial lesions prior to commencing the trial and 8 patients had to cease treatment on their trial lesions.

The psoriatic plaques were treated for 14 days. On each arm, one lesion was stripped prior to treatment (day 0) and again 7 days after the start of treatment (day 7). The plaques were stripped by repeated (10 times) application and removal of adhesive dressing. Each patient enrolled in the study had four lesions treated, two on each arm.

The PAI-2 or placebo gel was applied to the psoriatic lesions each evening. No dressing was used. The lesions on one arm were treated with 0.5 g (0.5 mL contained in a 2.5 mL syringe) placebo gel (1% w/v Natrosol gel). The lesions on the other arm were treated with PAI-2 gel (1.0 mg in 1% w/v Natrosol gel) in the same dose as the placebo. Each gel was applied to each lesion and rubbed in gently.

The PAI-2 gel was made by dissolving lmg/g of PAI-2 in a gel of 1% Natrosol, a partially substituted poly (hydroxyethyl) ether of cellulose. PAI-2 remains biologically active in this gel, and is released from this gel at a rate of 75% release in 6 hours.

PAI-2 itself may be produced as a highly purified recombinant protein obtained from fermentation of yeast cells transformed with cDNA encoding human PAI-2, for example by the methods described in U.S. Pat. No. 5,298,400, which is hereby incorporated by reference in its entirety. Methods of purifying PAI-2 are described, for example, in U.S. Pat. Nos. 5,204,807 and 5,462,857.

B. Safety & Tolerability

One goal of the study was to assess the safety and tolerability of topically applied PAI-2 gel. Of the 22 patients enrolled in the study, all patients, except one subject who did not continue the study after visit 1, were included in the safety analyses (n=21).

A complete hematological and biochemical screen was performed prior to treatment, at the end of treatment and at the end of the study. Full blood count, electrolytes, urea, creatinine, liver function tests and blood glucose were tested.

Any abnormal laboratory values, including post-treatment laboratory test, judged as clinically significant by the investigator, were to be followed up with appropriate medical management until there was a return to normal or baseline values.

Adverse events were monitored following one week of treatment (day 7), at the end of treatment (day 14) and at the end of the study (day 21). The investigator was responsible for recording all adverse events observed or recorded during the study, regardless of the drug-related assessment and/or clinical significance.

An adverse event (AE) was defined as any symptom, physical sign, syndrome or disease which either occurred during the study which was not present at baseline or if present at baseline, appeared to worsen during the study. This was regardless of the suspected cause of the event.

A serious adverse event (SAE) was defined as any event which was fatal or considered to be life threatening, which required or prolonged hospitalization or which caused permanent disability, a congenital abnormality, cancer or overdose.

Adverse events could be reported spontaneously by the patient, or in response to general questioning by the investigator or as a result of changes in laboratory values.

All adverse events were recorded. The duration, frequency (single episode, intermittent, continuous), severity (mild, moderate, severe—Table 1), an assessment of its cause (the underlying study indication, coexisting disease, concomitant medication, the study medication, or others), its relationship to the study medication (definite, probable, possible, unlikely, unrelated—Table 2 ), and the influence on the course of the study medication and its outcome were described.

At the commnencement of the study, patients were requested to report any adverse or unusual event/reaction during the study follow-up. In determining whether or not adverse events had occurred since the last visit, no suggestive question was to be asked other than "How have you been feeling since the last visit."

All adverse events persisting at the end of treatment were followed up until the event had either resolved or stabilized.

TABLE 1

Qualification of adverse event: assessment of severity

| | |
|---|---|
| MILD | Signs and symptoms, usually transient, requiring no special treatment and did not interfere with the subject's daily routine. |
| MODERATE | Symptoms of a sufficient severity to make patient uncomfortable; performance of daily activities may be influenced; patient was able to continue the study; treatment by simple therapeutic measures for the symptom may be needed |
| SEVERE | The adverse event resulted in alteration, discomfort or disability that was clearly damaging to the health. It forced the subject's withdrawal from the study. |

TABLE 2

Qualification of adverse event: assessment of casuality

| | |
|---|---|
| UNASSESSABLE | A report suggesting an AE, which cannot be judged because information is insufficient or contradictory and cannot be supplemented or verified |
| UNLIKELY/ UNRELATED | Temporal relationship to drug administration which makes a casual relationship improbable. Other drugs, chemicals or underlying disease provide plausible explanations. |
| POSSIBLE | Reasonable temporal relationship with drug treatment. Concurrent disease or other drugs or chemicals could also explain event. Information on drug withdrawal may be lacking or unclear |
| PROBABLE/ LIKELY | Reasonable temporal relationship with drug treatment. Unlikely to be attributed to concurrent disease or other drugs or chemicals, and follows a clinically reasonable response on withdrawal (dechallenge). Rechallenge information is not required to fulfil this definition. |
| CERTAIN | Plausible time relationship with drug treatment Concurrent disease or other drugs or chemicals cannot explain event. The response to withdrawal of the drug should be clinically plausible. The event must be definitive pharmacoligically or phenomenologically using a satisfactory re-challenge procedure if necessary and feasible |

Twenty one patients were eligible for the safety analysis. The specified total daily dose was 1 mg Natrosol-gel containing 1.0 mg/mL PAI-2 applied to two lesions, each treated with 0.5 mg. However, 19 patients were exposed to a half of the specified daily dose of PAI-2 for the first week of treatment, as they used one syringe instead of two on each arm, and 2 patients received specified daily treatment only for one week. Two patients out of 19 used one extra dose of medication at one occasion.

A total of 6 adverse events were reported in 5 patients during the study. One patient had elevated blood sugar level recorded at Visit 3 (day 14), of mild intensity, unlikely related to the study medication as judged by the investigator. A total of 5 skin related adverse events in 4 patients were reported during the study: cold sensation, slight tingling, burning and mild stinging on application of gel and itching/pain/cracking/bleeding on elbow.

Reported adverse events were not serious, occurred recurrently and were of mild to moderate severity. None of the adverse events required any action to be taken. The skin related adverse events (except itching/pain/cracking/bleeding) were considered to be related to the investigational products to some extent, though, the distribution of these events was similar between the test drug and placebo.

There were no serious adverse events reported. There were no deaths reported for this study. There were no other significant adverse events reported for this study.

Clinically significant changes in hematology and clinical chemistry were reported in 4 patients. No other values outside the reference range of clinical chemistry and haematology were clinically significant.

Patient No. 5 had elevated serum levels of ALT(SGPT) at baseline and at Visit 3 (123 U/L and 112 U/L, respectively) and elevated serum levels of GGT at baseline and Visit 3 (62 and 63 U/L, respectively). Since elevated liver function tests (ALT/GGT) were noted 18 months prior to the study start and at baseline and did not show tendency to rise during the study it could be concluded that these changes were not related to the study medication.

Patient No. 6 had elevated serum levels of SGOT (67 U/L), SGPT (124 U/L) and GGT (257 U/L) at baseline and at Visit 3 (71 U/L, 89 U/L and 237 U/L, respectively). These changes were deemed as not related to the study medication.

Patient No. 8 had decreased WBC counts ($2.0 \times 10^9$/L), Neutrophils ($0.95 \times 10^9$/L) and Lymphocites ($0.80 \times 10^9$/L) at baseline.

Patient No. 17 had decreased blood levels of Platelets ($82 \times 10^9$/L) at baseline, Visit 3 ($82 \times 10^9$/L) and at visit 4 ($85 \times 10^9$/L). Serum levels of GGT were elevated at baseline (227 U/L) and at Visit 4 (208 U/L). Blood glucose levels (BGL) were increased both at Visit 3 (11 mmol/L) and at Visit 4 (10.9 mmol/L). The change in BGL at Visit 3 was reported as an AE, judged as not related to the study medication.

The PAI-2 was measured in blood samples obtained prior to the treatment (visit 1), at the end of the treatment (visit 3) and at the end of the study (visit 4) using an ELISA method to determine whether systemic absorption occurred. The lower limit of detection for PAI-2 analysis was 8 ng/mL and the limit of quantitation (LOQ) was assumed to be around 50ng/mL. The accepted coefficient of variation (CV) between repeated analyses was 10% or less.

The PAI-2 levels in blood were measured using an ELISA method, to determine whether systemic absorption had occurred. A portion of the blood sample taken prior to treatment was stored at −80° C. and was to be used for detection of possible antibodies evoked by the PAI-2. One 20 mL-blood sample was collected from each patient prior to the treatment (visit 1), at the end of the treatment (visit 3) and at the end of the study (visit 4). The blood sample was divided in three separate tubes for PAI-2 analysis, haematology and clinical chemistry screen.

The PAI-2 levels detected in blood samples are shown in Table 3. The results, given in this table, represent analyses from different assays only if the results differ from one another where the results from both analyses are given.

The PAI-2 levels in samples obtained prior to the treatment were below the limit of detection (BDL) in all patients except in 4. The majority of blood samples collected at the end of the treatment and two weeks after the treatment had PAI-2 concentrations below limit of detection following two-week treatment and at the end of the treatment. However, the concentrations above the limit of detection were not at significant levels. In two patients analyses failed since the CV was greater than 10%. All results obtained in this study were below LOQ.

TABLE 3

PAI-2 ELISA results

| Patient number | PAI-2 concetrations (ng/mL)* | | |
|---|---|---|---|
| | Visit 1 | Visit 2 | Visit 3 |
| 01 | BDL | BDL | BDL |
| 02 | BDL | 12.1+ (CV =55.7%) | BDL 26.7 |
| 03 | BDL | | |
| 04 | BDL | BDL | BDL |
| 05 | BDL | BDL | |
| 06 | BDL | BDL | 14.0 BDL |
| 07 | 13.3 BDL | BDL | BDL |
| 08 | BDL | | |
| 09 | 11.1 BDL | 13.5 | |
| 10 | BDL | 13.3+ (CV =15.1%) | 26.0 BDL |
| 11 | BDL | BDL | BDL |
| 12 | BDL | 19.5 | 11.7 |
| 13 | 15.4 | 12.9 | 12.8 19.2 |
| 14 | BDL | BDL | BDL |
| 15 | BDL | BDL | BDL |
| 16 | BDL | BDL 20.7 | BDL |
| 17 | BDL | BDL | 16.0 19.6 |
| 18 | BDL | BDL | BDL 7.7 |
| 19 | BDL | BDL 8.6 | BDL |
| 20 | BDL | | |
| 21 | BDL | BDL | |
| 22 | 13.4 | BDL | 8.7 |

*LOQ = limit of quantitation (50 ng/mL); Shaded area = analyses not performed;
+CV > 10%; BDL = below limit of detection (<8 ng/mL);

In summary, the majority of adverse events were reported throughout the course of the study, although considered to be, to some extent, related to the investigational products, were similarly distributed between the test drug and placebo. Clinically significant changes in hematology and clinical chemistry found during the study were not related to the investigational products, as they were present at baseline.

There was an evidence of possible absorption of topically applied PAI-2 in some samples, however, the majority of samples had no detectable PAI-2 present. The detected PAI-2 concentrations were not at the significant levels as they were all below the LOQ which indicates that possible absorption of PAI-2, if any, is likely to be minimal.

Thus, the safety evaluation performed suggests that locally applied PAI-2 gel was well tolerated in patients with psoriasis.

C. Efficacy

Another goal of the study was to asses the efficacy of treating psoriasis with a PAI-2 gel. In accordance with this goal, at each visit changes in plaque thickness, degree of redness and scaling were assessed. In addition, a photograph of the lesions were taken prior to treatment, at the end of the treatment and at the end of the study.

1. Efficacy Measurements and Variables
a. Plaque Thickness

The thickness of the treated plaque was measured at Days 0, 7, 14 and 28 by the same person using Harpenden calipers. The thickness of the plaque was calculated by subtracting the thickness of a nearby area of normal skin from the thickness of the psoriatic lesion. The same area of normal skin was to be used at each assessment.

Assessments of plaque thickness were performed before and after stripping of the lesions at Days 0 and 7.

b. Redness and Scaling

At each visit (Days 0, 7, 14 and 28) the degree of redness was measured by using an erythema meter and assessed according to a categorical scale, graded 0 (none) to 3 (severe). The scaling of each lesion was assessed at each visit using the scale, graded 0 (none), 1 (mild), 2 (moderate) and 3 (severe).

Assessments of the degree of redness and scaling were performed before and after stripping of the lesions at Days 0 and 7.

c. Photographic Evidence

Photographs of the lesions were taken under standardized conditions by the hospital medical photographer prior to the treatment (day 0), at the end of the treatment (day 14) and at the end of the study (day 28). Photographs of the lesions were taken before and after stripping of the lesions at Day 0.

2. Efficacy Evaluation

Two study populations were defined prior to breaking the treatment code: Intention-to-treat (ITT) and Per Protocol (PP). The ITT group was used for the safety and efficacy analysis and the PP group used for the efficacy analysis, Day 0 to day 14.

The ITT population consisted of all subjects who received a dose of the study medication and had at least one efficacy observation recorded after treatment commenced (n=21).

The data obtained at visit 2 (Day 7) for patient No. 3 and patient No. 8, who received treatment only for one week, were carried forward to days 14 and 28 for ITT analysis.

The PP population comprised all subjects who completed visit 3 (day 14) and did not have significant protocol deviations as determined by the Principle Investigator (n=19).

Changes in plaque thickness and degree of redness/erythema and scaling were assessed at each visit and analyzed. Comparisons were made between active and placebo treatments, for stripped and unstripped lesions, and between stripped and unstripped within each treatment group. Changes over the time within each of the treatment subgroups were also examined.

a. Intention to Treat (ITT) Analyses (i) Plaque Thickness

The changes in plaque thickness from Day 0 to days 14 and 28 (in mm) are given in Table 4. Percentage change in plaque thickness for each treatment combination is given in Table 5.

There were no significant reductions in plaque thickness when analyzing the changes from Day 0 to days 14 and 28 except for one instance where the reduction in plaque thickness of unstripped lesions treated with the active drug was 27.24±43.7% from day 0 to day 14 (Table 5). However there was large variation in the percent change, including some large negative percent changes, indicating increases in size of plaque thickness.

TABLE 4

Plaque Thickness - Changes from Day 0 to Days 14 and 28 (mm)

| | Day 0–Day 14 | | | | Day 0–Day 28 | | | |
|---|---|---|---|---|---|---|---|---|
| | Unstripped | | Stripped | | Unstripped | | Stripped | |
| | Placebo | Active | Placebo | Active | Placebo | Active | Placebo | Active |
| Mean | 0.114 | 0.419 | 0.090 | 0.029 | 0.157 | 0.438 | 0.129 | 0.114 |
| SD | 0.373 | 1.184 | 0.409 | 0.203 | 0.304 | 1.227 | 0.349 | 0.259 |
| Median | 0.1 | 0.1 | 0 | 0 | 0.1 | 0 | 0.1 | 0.1 |
| Min | −0.4 | −0.2 | −0.7 | −0.4 | −0.4 | −0.3 | −0.3 | −0.4 |
| Max | 0.9 | 5.0 | 1.1 | 0.4 | 0.9 | 5.2 | 1.1 | 0.8 |
| p value* | 0.176 | 0.121 | 0.322 | 0.526 | 0.028 | 0.118 | 0.107 | 0.057 |

*paired t-test

TABLE 5

Change in plaque thickness from Day 0 to Days 14 and 28 for each treatment combination (percentage)

| | Day 0–Day 14 | | | | Day 0–Day 28 | | | |
|---|---|---|---|---|---|---|---|---|
| | Unstripped | | Stripped | | Unstripped | | Stripped | |
| | Placebo | Active | Placebo | Active | Placebo | Active | Placebo | Active |
| Mean % | −4.55 | 27.24* | −13.65 | −6.03 | 22.19 | 9.85 | 6.27 | 9.60 |
| SD | 95.5 | 43.7 | 95.0 | 85.1 | 57.9 | 72.3 | 80.7 | 96.3 |
| Median (%) | 25 | 25 | 0 | 0 | 33.3 | 0 | 20 | 25 |
| Min (%) | −300 | −50 | −200 | −300 | −133.3 | −200 | −200 | −300 |
| Max (%) | 100.0 | 100 | 100 | 100 | 100 | 94.5 | 100 | 100 |
| p value+ | 0.829 | 0.01* | 0.518 | 0.749 | 0.095 | 0.539 | 0.725 | 0.653 |

+paired t-test;
*significant change;
N.B. A negative number indicates an increase (ii) Redness Changes in score of redness, assessed according to the scale graded from 0 (none) to 3 (severe), from day 0 to Days 14 and 28, are given in Table 6.

Changes in score of redness were not significant except for one instance where p-value came close to significance (p=0.022) and that was for lesions treated with placebo, changes from Day 0 to day 28, unstripped (−0.048±0.7) vs. stripped (0.524±0.81).

There was also significant decrease in redness of stripped lesions in the active group when analyzing the changes from Day 0 to Day 14 where the p-value was 0.016 using paired t-tests. Comparing Day 0 to day 28, there was significant decrease in redness in the placebo group where the p-value was 0.008 (Table 6).

(iv) Scaliness

Changes in score, assessed according to the scale graded 0 (none), 1 (mild), 2 (moderated) and 3 (severe), from Day 0 to Days 14 and 28 are given in Tables 8–9.

There were no significant differences in any comparisons made for this parameter.

TABLE 6

Redness - Changes in score from Day 0 to Days 14 and 28

| | Day 0–Day 14 | | | | Day 0–Day 28 | | | |
|---|---|---|---|---|---|---|---|---|
| | Unstripped | | Stripped | | Unstripped | | Stripped | |
| | Placebo | Active | Placebo | Active | Placebo | Active | Placebo | Active |
| Mean | −0.190 | −0.095 | 0.286 | 0.333 | −0.048 | 0.143 | 0.524 | 0.286 |
| SD | 0.680 | 0.700 | 0.717 | 0.577 | 0.740 | 0.655 | 0.814 | 0.784 |
| Median | 0 | 0 | 0 | 0 | 0 | 0 | 1 | 0 |
| Min | −1 | −1 | −1 | −1 | −1 | −1 | −1 | −1 |
| Max | 1 | 1 | 1 | 1 | 1 | 1 | 2 | 1 |
| p value[+] | 0.214 | 0.54 | 0.083 | 0.016* | 0.771 | 0.329 | 0.008* | 0.11 |

[+]paired t-tests;
*statistically significant (iii) Erythema

Erythema was measured by using an erythema meter. Changes in erythema from Day 0 to Days 14 and 28 are given in Table 7.

There were no significant changes when comparing changes from day 0 to Days 14 and 28 when placebo treatment was compared with active treatment. However, there were significant decrease when analyzing the changes from baseline within each treatment subgroup using paired t-tests (Table 7).

TABLE 7

Erythema - Changes from Day 0 to Days 14 and 28

| | Day 0–Day 14 | | | | Day 0–Day 28 | | | |
|---|---|---|---|---|---|---|---|---|
| | Unstripped | | Stripped | | Unstripped | | Stripped | |
| | Placebo | Active | Placebo | Active | Placebo | Active | Placebo | Active |
| Mean | −2.190 | 33.000 | 31.000* | 33.619 | −1.429 | 38.762* | 33.857 | 36.619 |
| SD | 61.355 | 59.756 | 53.329 | 67.528 | 64.485 | 59.490 | 69.013 | 66.419 |
| Median | −2 | 39 | 23 | 41 | 10 | 36 | 23 | 39 |
| Min | −96 | −87 | −52 | −126 | −122 | −87 | −90 | −95 |
| Max | 152 | 164 | 167 | 134 | 84 | 154 | 212 | 208 |
| p value[+] | 0.872 | 0.02** | 0.015* | 0.034 | 0.92 | 0.007* | 0.036 | 0.02** |

[+]paired t-tests;
*statistically significant;
**borderline significance

TABLE 8

Scaliness - Changes in score from Day 0 to Days 14 and 28

|  | Day 0–Day 14 | | | | Day 0–Day 28 | | | |
| --- | --- | --- | --- | --- | --- | --- | --- | --- |
|  | Unstripped | | Stripped | | Unstripped | | Stripped | |
|  | Placebo | Active | Placebo | Active | Placebo | Active | Placebo | Active |
| Mean | −0.381 | 0.000 | −0.048 | −0.238 | 0.048 | 0.048 | 0.048 | −0.143 |
| SD | 1.024 | 0.775 | 1.024 | 1.091 | 1.071 | 0.921 | 1.071 | 0.910 |
| Median | −1 | 0 | 0 | 0 | 0 | 0 | 0 | 0 |
| Min | −2 | −1 | −2 | −2 | −2 | −2 | −2 | −2 |
| Max | 2 | 2 | 2 | 3 | 2 | 2 | −2 | 2 |
| p value+ | 0.104 | 1.0 | 0.833 | 0.329 | 0.841 | 0.815 | 0.841 | 0.48 |

+paired t-tests

TABLE 9

|  | p-valve | |
| --- | --- | --- |
| Comparison | Day 0 to 14 | Day 0 to 28 |
| Unstripped, placebo vs active | 0.181 | 1.000 |
| Stripped, placebo vs active | 0.563 | 0.538 |
| Placebo, unstripped vs stripped | 0.298 | 1.000 |
| Active, unstripped vs stripped | 0.420 | 0.504 | b. Per Protocol (PP) Analyses

Nineteen (19) patients were evaluable for PP analyses of efficacy. There were no significant differences in any of PP analyses performed except for the plaque thickness where the reduction in plaque thickness of unstripped lesions treated with the active drug was 28.36±45.6% (Table 10).

TABLE 10

Change in plaque thickness from Day 0 to Day 14 for each treatment combination (percentage).

|  | Day 0–Day 14 | | | |
| --- | --- | --- | --- | --- |
|  | Unstripped | | Stripped | |
|  | Placebo | Active | Placebo | Active |
| Mean (%) | −7.92 | 28.36* | 3.33 | 9.12 |
| St. Dev. | 98.7 | 45.6 | 82.2 | 54.8 |
| Median (%) | 25 | 25 | 0 | 0 |
| Min (%) | −300 | −50 | −200 | −100 |
| Max (%) | 100 | 100 | 100 | 100 |
| p value+ | 0.731 | 0.014* | 0.862 | 0.477 |

+paired t-tests; *Significant difference; N.B. A negative number indicates an increase 3. Statistical/analytical issues Two sample t-tests were performed to compare the changes between treatment subgroups for the 4 factors (plaque thickness, redness, erythema and scaliness) from Day 0 to Day 14 and Day 28 respectively, using the scales, graded 0 (none) to 3 (severe), for redness and scaliness as continuous variables. Erythema was measured by using an erythema meter. In each case the Day 14 and 28 measurements were subtracted from Day 0 (so that a positive difference indicates a reduction over time), and the differences compared between the following groups:

Unstripped, placebo vs. active
Stripped, placebo vs. active
Placebo, unstripped vs. stripped
Active, unstripped vs. stripped Paired t-tests also were performed to examine changes over time within each treatment subgroup, testing the hypothesis that the change from baseline is zero within that particular subgroup.

The percentage change for plaque thickness was calculated for each time period as the difference between Day 0 and Days 14 and 28, divided by Day 0 and multiplied by 100.

Pair-wise comparisons were made within the four treatment subgroups. Accordingly, conclusions can only be made on the differences from baseline within that subgroup, and not between treatment groups.

4. Efficacy conclusions

There were no significant differences when comparing changes from Day 0 to Days 14 and 28, in any of the following comparisons:

unstripped, placebo vs. active
stripped, placebo vs. active
placebo, unstripped vs. stripped
active, unstripped vs. stripped for the four parameters measured (i.e. plaque thickness, redness, erythema and scaliness) at the α=0.02 (one-sided probability) level, as specified in the protocol.

However, there was one instance where the p value came close to significance (p=0.022), and that was for redness in the ITT population, Day 0–28, placebo, unstripped (−0.048±0.7) vs. stripped (0.524±0.81).

5. Paired comparisons within each treatment group

There was one instance where the reduction in plaque thickness exceeded 25%, and that was in the unstripped, active subgroup, day 0 to Day 14. In the ITT population the percent reduction was 27.24±43.7 and in the per protocol group 28.36±45.6. These differences were significant when tested using paired t-tests within the group, at p=0.01 and p=0.014, respectively. However a large variation in the percent change was observed, including some large negative percent changes, which indicate increases in size of plaque thickness.

There were also significant reductions in redness and erythema when analyzing the changes from baseline within each treatment subgroup, using paired t-tests. These significant changes were all reductions from baseline, and all in the ITT population.

D. Discussion and Overall Conclusions

Clinically significant changes in hematology and clinical chemistry found in this study were not considered to be associated with the study medication indicating that the systemic side effects are likely to be minimal, if not non existent.

A number of skin reactions on application were recorded in this study. The majority of these events although considered to be, to some extent, related to the investigational products were similarly distributed between the test drug and placebo Prior experience in healthy volunteers using PAI-2 from the same batch and at the same strength, as used in this study, showed that the drug was well tolerated without any positive skin reactions either to PAI-2 or buffer. That finding together with the fact that the distribution of skin reactions in the present study was similar between placebo and active treatment indicate that local application of PAI-2 gel is likely to be well tolerated. However, long term safety study in a larger group of patients should be conducted to evaluate the rate of occurrence of skin reactions in patients with psoriases.

There are no conclusive data of absorption and systemic distribution of topically applied PAI-2 since the majority of samples obtained at the end of treatment and two weeks after the treatment had no detectable PAI-2 present Efficacy data of topically applied PAI-2 gel in healing psoriatic lesions were obtained from the analyses of changes in plaque thickness, redness/erythema and scaling. It was shown that the reduction in plaque thickness of unstripped lesions was more than 25% following two weeks of treatment with the active drug (Tables 5 and 10). Furthermore, there also was significant reduction in redness of stripped lesions following two weeks of active treatment. There also was significant reduction in redness and erythema when analyzing the changes from baseline within each treatment subgroup, using paired t-tests (Tables 6 and 7). However, there were no significant differences when comparing unstripped and stripped lesions for the four parameters measured.

It should be noted that a large variation in the percent change of plaque thickness was found (Table 5). This could be partially explained by the variation in results between plaque thickness and skin thickness due to the inaccurate method used for measurement of thickness (Harpenden calipers), deviations in measurements and operator variability.

In sum, safety evaluation performed in this study suggests that locally applied PAI-2 gel was well tolerated in patients with psoriasis. Efficacy data indicate that PAI-2, topically applied to psoriatic lesions, is likely to have a protective role in cutaneous pathologies eliciting wound healing and can be of benefit in therapy of psoriasis.

EXAMPLE 2

Preparation of PAI-2-Containing Gels and Measurement of PAI-2 Release

In these experiments, the PAI-2 containing gel was placed in the top chamber of a two compartment vessel. The bottom chamber contained buffer, and the two chambers were separated by a microporous membrane. The appearance of PAI-2 in the lower chamber indicated PAI-2 release from the gel, and was monitored by assays for PAI-2 activity.

The table below reflects the improved properties of the new PAI-2 gel formulations. The enhanced released of PAI-2 from the gel is depicted in FIG. 1.

CLARITY OF PAI-2 GEL FORMULATIONS

| Polymer | Conc. (%) | Excipients Placebo | None | Genapol PFIO | Tween 80 |
|---|---|---|---|---|---|
| Carbopol 971P | 0.5 | clear | s.o. | clear | clear |
|  | 1.0 | clear | s.o. | clear | clear |
| Carbopol 974P | 0.5 | clear | opal | s.o. | s.o. |
|  | 1.0 | clear | cloudy | opal. | s.o. |
| Carbopol 981 | 0.5 | clear | s.o. | clear | clear |
|  | 1.0 | clear | s.o. | clear | clear |
| Bianose 7LF | 2.0 | clear | cloudy[d] | v.o.[d] | opal.[d] |
| Natrosol 25OHHX | 1.5 | clear | s.o. | clear | clear |
| Keltrol RD | 3.0 | opal. | cloudy | v.o. | cloudy |

Key:
opal. = opalescent
s.o. = slightly opalescent
v.o. = very opalescent
[d] = possible microbial contamination Methods Polymers were dissolved to the desired concentration, and then titrated to pH 7.4–7.7. Detergents were added to 0.05% and PAI-2 to 1 mg/ml. Sodium azide (0.05%) was used as a preservative.

The invention described herein may be embodied in other specific forms without departing from the spirit or essential characteristics thereof. The specific embodiments previously described are therefore to be considered as illustrative of, and not limiting, the scope of the invention. Additionally, the disclosure of all publications cited above are expressly incorporated herein by reference in their entireties to the same extent as if each were incorporated by reference individually.

We claim:

1. A method of treating psoriasis comprising administering to a patient in need thereof an effective amount of a urokinase inhibitor selected from the group consisting of PAI-2, a variant thereof having plasminogen activating inhibitory properties, a derivative of PAI-2, and a variant of said derivative, wherein said inhibitor is topically administered to the affected area of the skin.

2. The method according to claim 1, wherein said protease inhibitor is administered in a gel formulation.

3. The method according to claim 2, wherein said gel is a cellulose gel further comprising a detergent.

4. The method according to claim 3, wherein said detergent is Tween-80.

5. The method according to claim 3, wherein said gel further comprises propylene glycol.

6. A method of treating psoriasis comprising administering to a patient in need thereof an effective amount of a therapeutic agent comprising PAI-2 and at least one other serine protease inhibitor, wherein said therapeutic agent is topically administered to the affected area of the skin.

7. The method according to claim 6, wherein said other serine protease inhibitor is a uPA inhibitor.

8. The method according to claim 6, wherein said therapeutic agent further comprises a protease inhibitor selected from the group consisting of thiol protease inhibitors, acid protease inhibitors, and metalloproteinase inhibitors.

9. The method according to claim 6, wherein said protease inhibitors are co-administered with PAI-2.

10. A pharmaceutical composition comprising PAI-2 in a gel containing a detergent.

11. A pharmaceutical composition according to claim 10, wherein said detergent is Tween-80, and said gel is a cellulose gel.

12. A pharmaceutical composition comprising PAI-2 and at least one other serine protease inhibitor.

13. A pharmaceutical composition according to claim 12 further comprising a protease inhibitor selected from the group consisting of thiol protease inhibitors, acid protease inhibitors, and inetalloproteinase inhibitors.

14. A pharmaceutical composition according to claim 12, wherein said composition is in the form of a cellulose gel that comprises a detergent.

15. The method of claim 1, wherein said PAI-2 is administered in a range of 0.1–2000 $\mu g/cm^2$ of psoriatic plaque.

16. The method according to claim 15, wherein said PAI-2 is administered at least once a day for at least five days.

17. The method of claim 1, wherein said derivative thereof is obtained by biochemical modification of PAI-2, wherein said modification is selected from the group consisting of chemical linking with polyethylene glycol, phosphate group attachment, sulfate group attachment, peptidase treatment, treatment with a sugar chain-modifying enzyme, and treatment with a sugar attachment enzyme.

18. The method of claim 1, wherein said variant is obtained by deletion or addition of amino acid residues from the amino terminal end of PAI-2.

19. The method of claim 1, wherein said variant is obtained by deletion or addition of amino acid residues from the carboxy terminal end of PAI-2.

20. The method according to claim 16, wherein said PAI-2 is administered at least once a day for at least fourteen days.

* * * * *